(12) United States Patent
Wolosuk

(10) Patent No.: US 8,608,032 B2
(45) Date of Patent: Dec. 17, 2013

(54) DISPENSER

(76) Inventor: Susan M. Wolosuk, Yale, VA (US)

( * ) Notice: Subject to any disclaimer, the term of this patent is extended or adjusted under 35 U.S.C. 154(b) by 537 days.

(21) Appl. No.: 12/957,579

(22) Filed: Dec. 1, 2010

(65) Prior Publication Data

US 2011/0073675 A1 Mar. 31, 2011

Related U.S. Application Data

(63) Continuation-in-part of application No. 12/150,795, filed on May 1, 2008, now abandoned.

(51) Int. Cl.
| B67D 7/84 | (2010.01) |
| G04C 23/00 | (2006.01) |
| G05D 7/00 | (2006.01) |
| G04C 23/42 | (2006.01) |
| B05B 3/00 | (2006.01) |

(52) U.S. Cl.
USPC ........... 222/160; 222/167; 222/168; 222/645; 222/646; 222/649; 239/227

(58) Field of Classification Search
USPC ......... 222/160, 164, 167, 168, 169, 504, 638, 222/645–649; 239/227, 263.1, 263.3, 264, 239/67–70
See application file for complete search history.

(56) References Cited

U.S. PATENT DOCUMENTS

| 3,061,149 | A | * | 10/1962 | Bystrom | 222/167 |
| 3,127,065 | A | * | 3/1964 | Stevenson | 222/164 |
| 5,895,318 | A | * | 4/1999 | Smrt | 454/256 |
| 6,216,925 | B1 | * | 4/2001 | Garon | 222/645 |
| 6,419,122 | B1 | * | 7/2002 | Chown | 222/162 |
| 7,337,989 | B1 | * | 3/2008 | Penner et al. | 239/263.1 |
| 7,427,038 | B2 | * | 9/2008 | Wang et al. | 239/240 |
| 7,837,132 | B2 | * | 11/2010 | Mazooji et al. | 239/263.1 |
| 8,079,498 | B2 | * | 12/2011 | Anderson et al. | 222/183 |
| 2004/0089329 | A1 | * | 5/2004 | Bijster | 134/167 R |
| 2008/0018995 | A1 | * | 1/2008 | Baun | 359/399 |
| 2008/0212176 | A1 | * | 9/2008 | Baun et al. | 359/429 |

FOREIGN PATENT DOCUMENTS

WO WO 9736697 A1 * 10/1997 .............. B08B 9/00

* cited by examiner

*Primary Examiner* — Paul R Durand
*Assistant Examiner* — Benjamin R Shaw
(74) *Attorney, Agent, or Firm* — Dale J. Ream

(57) ABSTRACT

A disinfectant dispenser includes a rotating assembly coupled to a base and rotatable thereabout and a first motor operatively coupled to the rotating assembly for rotation thereof when activated. A carriage is pivotally mounted to an upper portion of the rotating assembly and movable between vertical and horizontal configurations. A second motor is operatively connected to the carriage for moving the carriage between the vertical and horizontal configurations. A control unit is electrically connected to the power source and motors and includes programming for activation thereof. A delivery unit configured to hold a propellant container is attached to the carriage, the delivery unit defining an outlet to dispense the propellant when activated. A solenoid is positioned proximate the delivery unit so as to activate the propellant when the solenoid is actuated.

13 Claims, 6 Drawing Sheets

DISPENSER

CROSS REFERENCE TO RELATED APPLICATIONS

The present application is a continuation-in-part of U.S. patent application Ser. No. 12/150,795, filed May 1, 2008 now abandoned and titled "Disinfectant Household Bomb," the disclosure of which is incorporated herein by reference.

BACKGROUND OF THE INVENTION

This invention relates generally to a household disinfectant bomb and, more particularly, to a rotary and elevation changing disinfectant dispenser.

Insect fogger products are well known for dispensing an insect killing fog within a selected room. Such products include pressurized pesticides that are dispersed from an aerosol can across a room when activated. Although assumably effective for their intended purposes, insect fogger products and prior patent proposals do not provide for full or even coverage of a room, do not dispense disinfectant and anti-germicide compositions, and do not provide the user-friendly features that are desired by consumers. Specifically, the existing insect fogger products typically spray a fog in a generally upward direction that does not maximize the potential for the insecticide to reach all portions of the room. This may be because these products utilize a wide angle spray pattern that disperses only a small amount of pesticide in any single direction.

Therefore, it would be desirable to have a dispenser that generates a focused spray while both rotating and pivoting to provide even coverage of both high and low points of a room. Further, it would be desirable to have a dispenser that enables a user to activate a selected dispensing cycle and to set a delay before activation begins. In addition, it would be desirable to have a disinfectant dispenser that dispenses antibacterial or anti-germicide chemicals.

SUMMARY OF THE INVENTION

A dispenser according to a preferred embodiment of the present invention includes a rotating assembly coupled to a fixed base that is rotatable thereabout and a first motor operatively coupled to the rotating assembly for activation thereof. A carriage is pivotally mounted to an upper portion of the rotating assembly and movable between vertical and horizontal configurations. A second motor is operatively connected to the carriage for moving the carriage between the vertical and horizontal configurations. A control unit is electrically connected to a power source and motors and includes programming for activation thereof. A delivery unit configured to hold a propellant container is attached to the carriage, the delivery unit defining an outlet or nozzle to dispense the propellant when activated. A solenoid is positioned proximate the delivery unit so as to activate the propellant when the solenoid is actuated.

Therefore, a general object of this invention is to provide a dispenser for delivering a disinfectant chemical through the air of a room so as to clean and kill germs therein.

Another object of this invention is to provide a dispenser, as aforesaid, having a delivery unit configured to hold a prepackaged pressurized disinfectant container that will dispense its contents when activated.

Still another object of this invention is to provide a dispenser, as aforesaid, having a rotating portion that moves the dispenser unit in a circular pattern as it delivers its pressurized contents.

Yet another object of this invention is to provide a dispenser, as aforesaid, having a carriage that is pivotally mounted atop the rotating assembly that pivots the delivery unit between vertical and horizontal configurations as the delivery unit delivers its pressurized contents.

A further object of this invention is to provide a dispenser, as aforesaid, having first and second motors for moving the rotating assembly and carriage, respectively, when activated.

A still further object of this invention is to provide a dispenser, as aforesaid, having a control unit that selectively delays a user-initiated activation to enable the user to exit the room prior to activation.

A particular object of this invention is to provide a dispenser, as aforesaid, that is easy to use and cost-effective to manufacture.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 4a is another side angle of the dispenser as in FIG. 3b;

FIG. 4b is a sectional view taken along line 4b-4b of FIG. 4a;

DESCRIPTION OF THE PREFERRED EMBODIMENT

Figure 1:
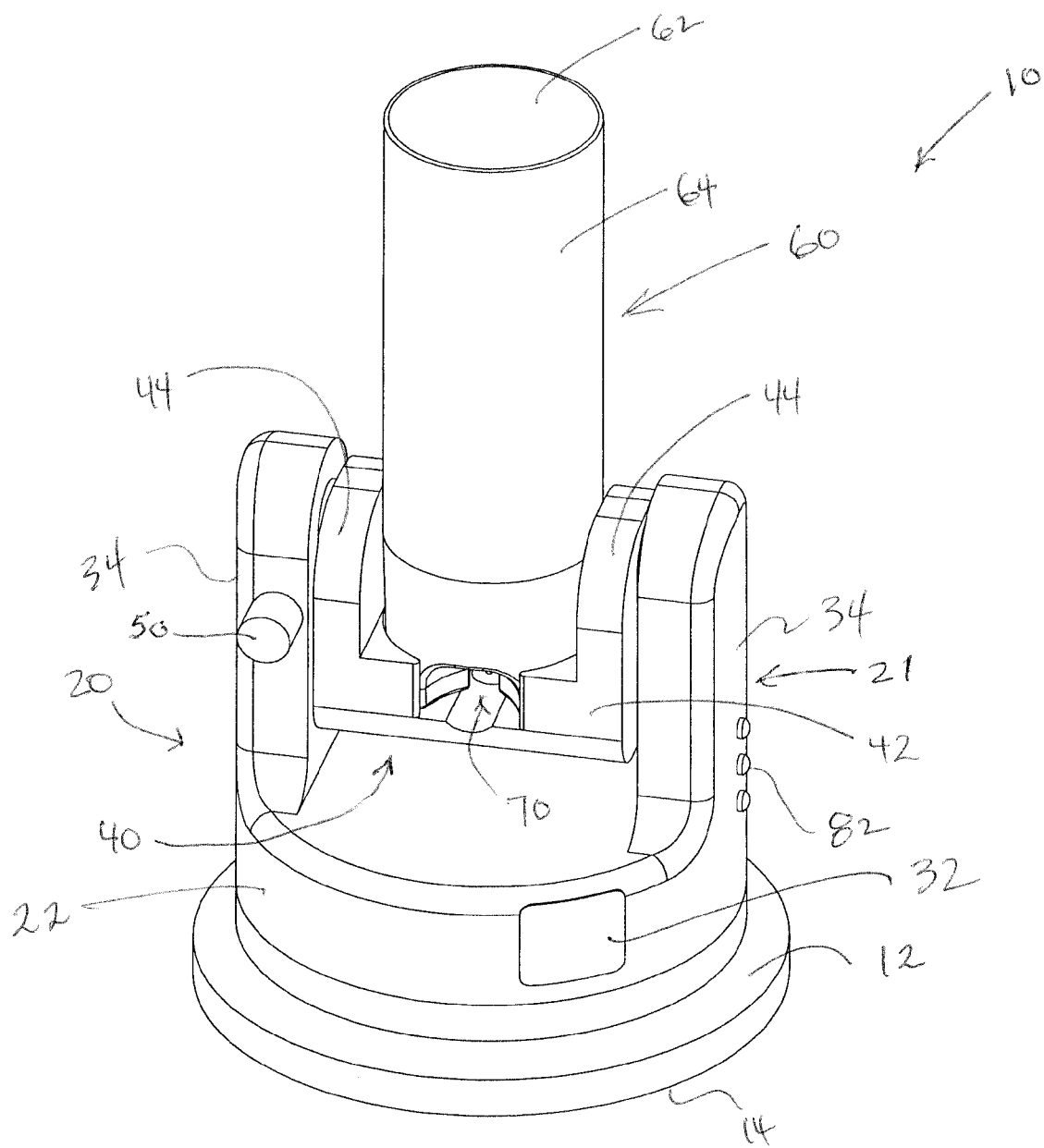
FIG. 1 is a perspective view of a dispenser according to a preferred embodiment of the present invention.

A rotary and elevation changing dispenser according to a preferred embodiment of the present invention will now be described with reference to FIGS. 1 to 6 of the accompanying drawings. The dispenser 10 includes a rotating assembly 20 coupled to a stationary base 12, a carriage 40 pivotally coupled to the rotating assembly 20, and a delivery unit 60 mounted atop the carriage 40 and configured to selectively dispense a propellant into the air. First 28 and second 50 motors are operatively connected to the rotating assembly 20 and carriage 40, respectively, for moving the assembly 20 and carriage 40 in a prescribed manner as the propellant is dispursed, as will be described in greater detail below.

The dispenser 10 includes a stationary base 12 preferably having a circular configuration although many other geometric configurations would also work. The base 12 includes a flat bottom surface 14 that provides stability to the dispenser 10 when situated atop a flat surface such as a table, chair, or floor. The base 12 includes an upper surface 16 generally parallel to the base bottom surface 14, the base 12 including a shaft 18 fixedly attached to the base upper surface 16 and extending upwardly therefrom (FIGS. 4c and 4d).

The rotating assembly 20 includes a lower portion 22 having a bottom end 24 rotationally coupled to the base 12. More particularly, the bottom end 24 of the rotating assembly 20 includes a recessed area having a configuration that is complementary to that of the shaft 18 and includes bearings 26 for engaging the shaft 18 for rotation thereabout (FIG. 4c). The rotating assembly 20 includes a first motor 28 mounted proximate the bottom end 24 of the lower portion 22, a gear 30 being operatively connected to the first motor 28 and to the shaft 18 for rotating the lower portion 22 when the first motor 28 is activated/energized. The lower portion 22 of the rotating assembly 20 includes a battery compartment 32 in which a battery power source 33 may be positioned, the first motor 28 being electrically connected to the battery 34. The rotating assembly 20 includes an upper portion 21 having a pair of spaced apart support arms 34 extending upwardly from an upper end of the lower portion 22. Interior surfaces proximate upper ends of the support arms 34 define respective recesses 36 or similar operative structures for coupling with the carriage 40 as described below.

The carriage 40, which may also be referred to as an elevation carriage 40 includes a body portion 42 and a pair of divergent fasteners 44 extending upwardly from the carriage body portion 42 (FIG. 1). Preferably, the fasteners 44 are generally parallel to one another and perpendicular to an upper surface of the body portion 42. Further, an outer aspect of each fastener 44 includes a flange 46 that extends outwardly into a respective support arm recess 36 (FIG. 4b), said flange/recess combinations being configured to allow the carriage 40 to pivot therein between vertical and horizontal configurations. The scope of movement is best understood by viewing the fasteners 44 in FIGS. 3a and 3b. The pivotal movement is even better understood by considering the position of the delivery unit 60 in FIGS. 3a and 3b as will be further described below. A limit switch 48 may be positioned in a respective recess 36 and configured to halt pivotal movement of a respective fastener flange 46 when the delivery unit 60 reaches a substantially horizontal configuration as such a configuration indicates the end of a disinfectant dispensing operation as will be described in more detail later.

Figures 4A, 4B:
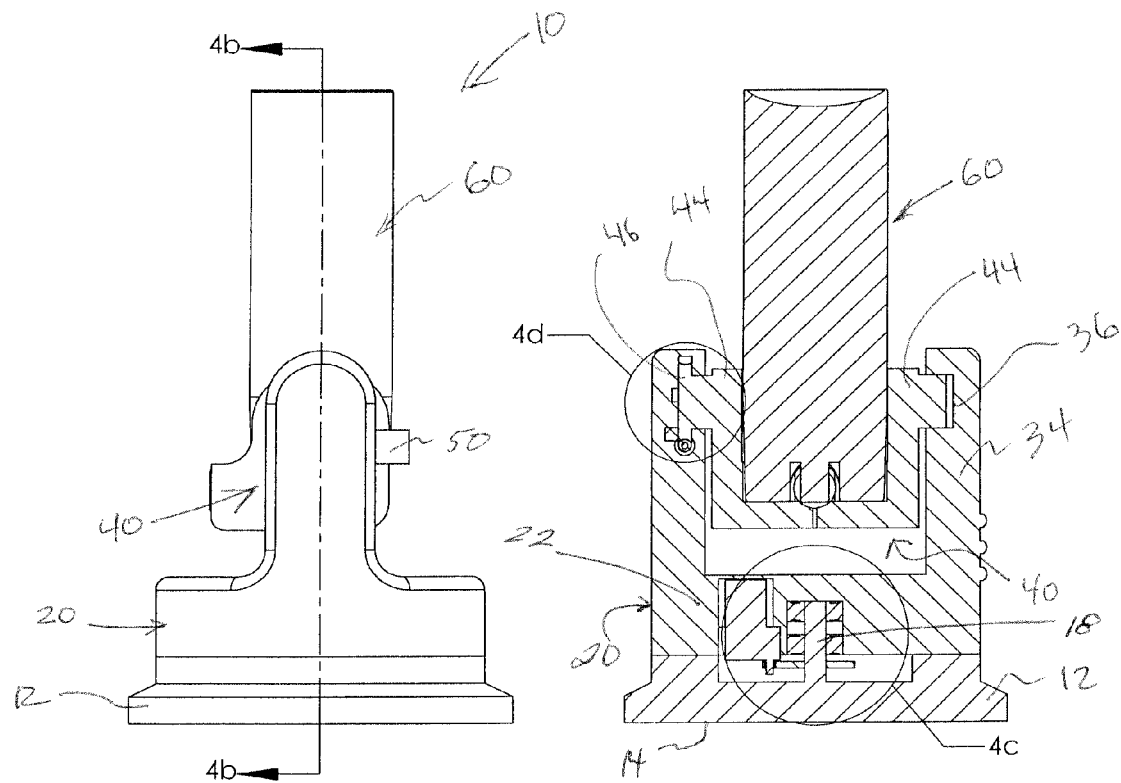
Figures 4C, 4D:
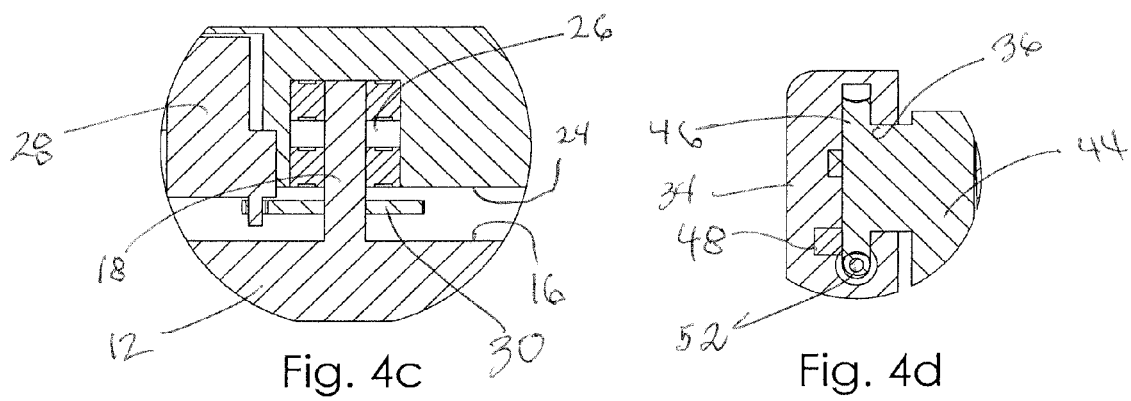
FIG. 4c is an isolated view on an enlarged scale taken from a portion of FIG. 4b.
FIG. 4d is a an isolated view on an enlarged scale taken from a portion of FIG. 4b.

A second motor 50, which may also be referred to as an elevation carriage motor, may be situated in a respective support arm 34 and is operatively coupled to a respective carriage fastener flange 46 by a gear 52 such as a worm gear or the like (FIG. 4d). When activated, the second motor 50 causes the carriage 40 to pivot along the imaginary center axis that extends between the support arm recesses 36.

The delivery unit 60 is a tubular container having a closed upper end 62 with an upstanding side wall 64 that defines an interior area (not shown) (FIG. 1). The interior area includes a configuration suitable to receive and hold a propellant, such as a prepackaged disinfectant canister (not shown) under pressure that must be activated in order to disburse its disinfectant contents. The delivery unit side wall 64 defines an aperture 66 in communication with the interior area. The prepackaged disinfectant canister is preferably loaded into the delivery unit 60 to rest near the aperture 66. It is understood that the delivery unit 60 may be removed from the carriage 40, a disinfectant canister positioned therein, and re-coupled to the carriage, such as with a snap fit arrangement or other fasteners. Alternatively, the entire delivery unit 60 may be pre-packaged and disposable after use. A solenoid 68 is positioned on the carriage body portion 42 (FIG. 2), is electrically connected to the battery 34, and is aligned to extend through the aperture 66 and into the interior area when activated so as to actuate the disinfectant canister. Opposite the aperture 66, the delivery unit 60 includes an outlet 70 (preferably including a nozzle) operatively connected to a disinfectant canister and configured to disburse its contents, as will be described further below. The solenoid 68 is movable between a retracted configuration outside the delivery unit interior area and an extended configuration extending into the interior area so as to actuate the disinfectant canister to disburse disinfectant through the delivery unit outlet/nozzle 70.

Figure 5:
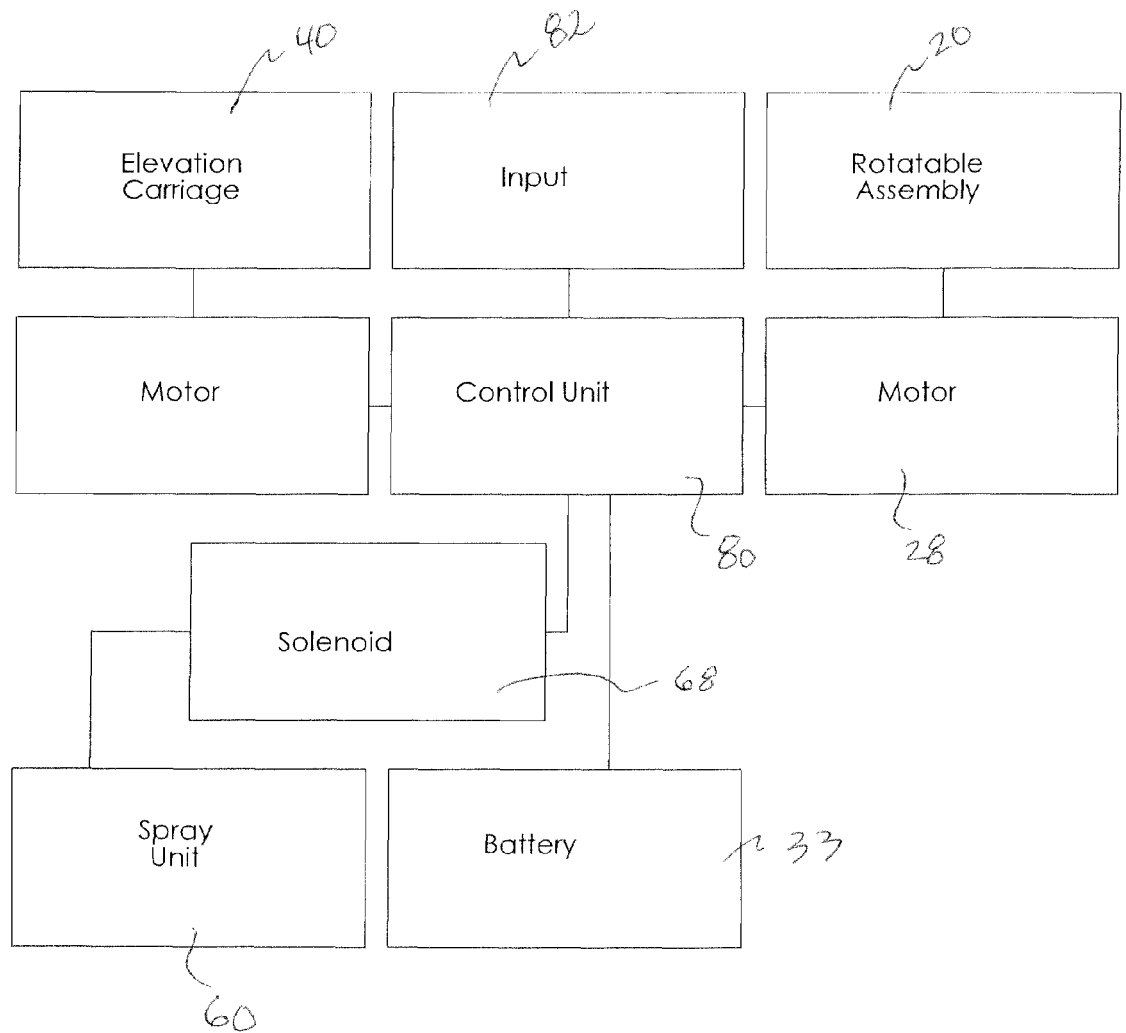
FIG. 5 is a block diagram of the electronic components of the disinfectant dispenser according to the present invention.

The disinfectant dispenser 10 includes a control unit 80 and an input 82 electrically connected thereto (FIG. 5). The input 82 may be one or more buttons positioned on one of the rotating assembly support arms 34 (FIG. 1). The control unit 80 may include programming or circuitry for controlling the setting of various parameters regarding a disinfectant dispensing cycle as will be described below according to an exemplary embodiment of the present invention.

Figure 6:
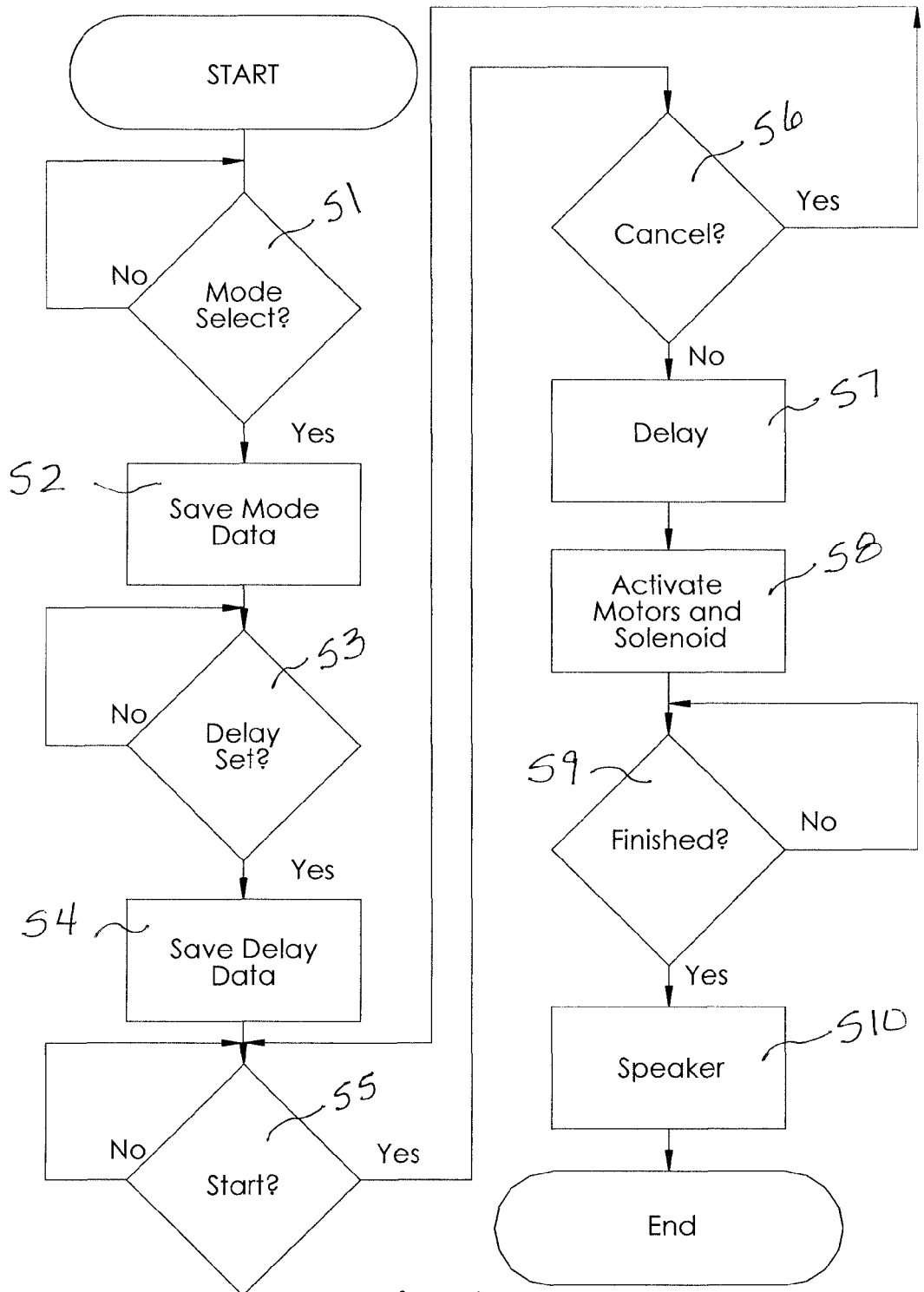
FIG. 6 is a flowchart illustrating the logic performed by the control unit.
Figure 1:
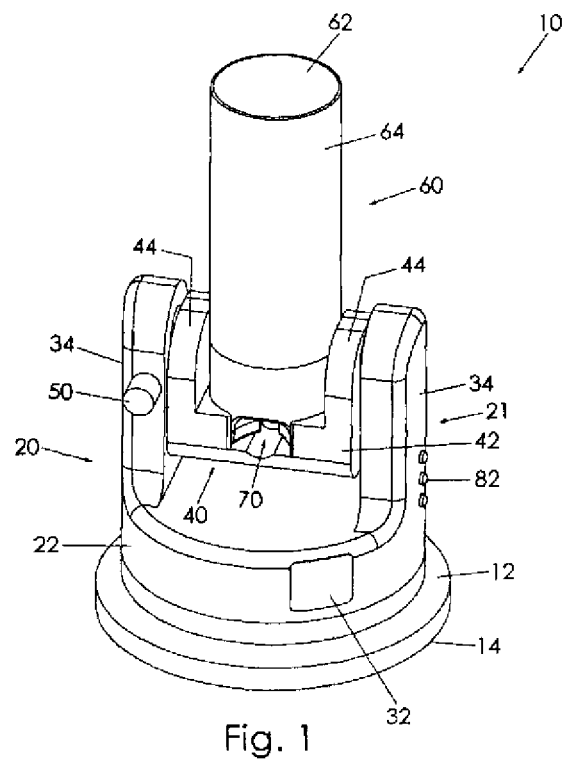
Figure 2:
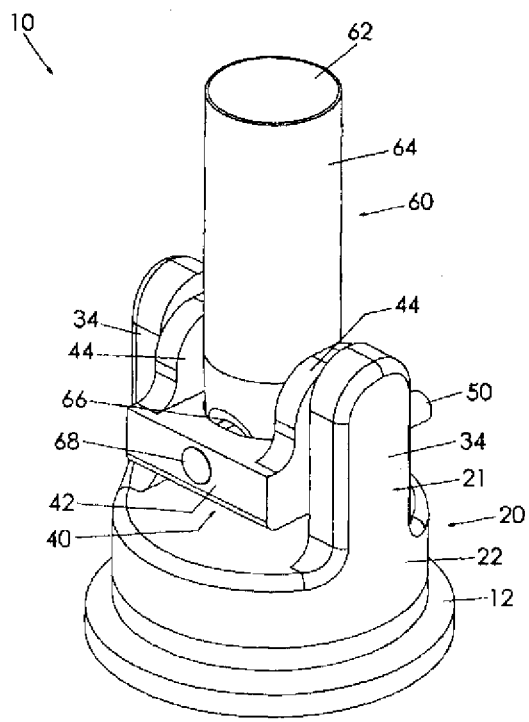
Figure 3A:
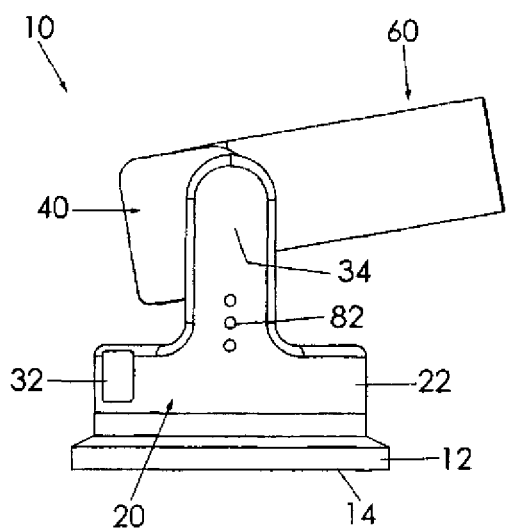
Figure 3B:
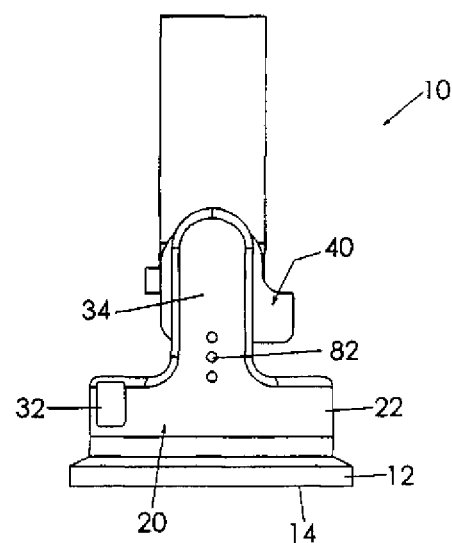
Figure 5:
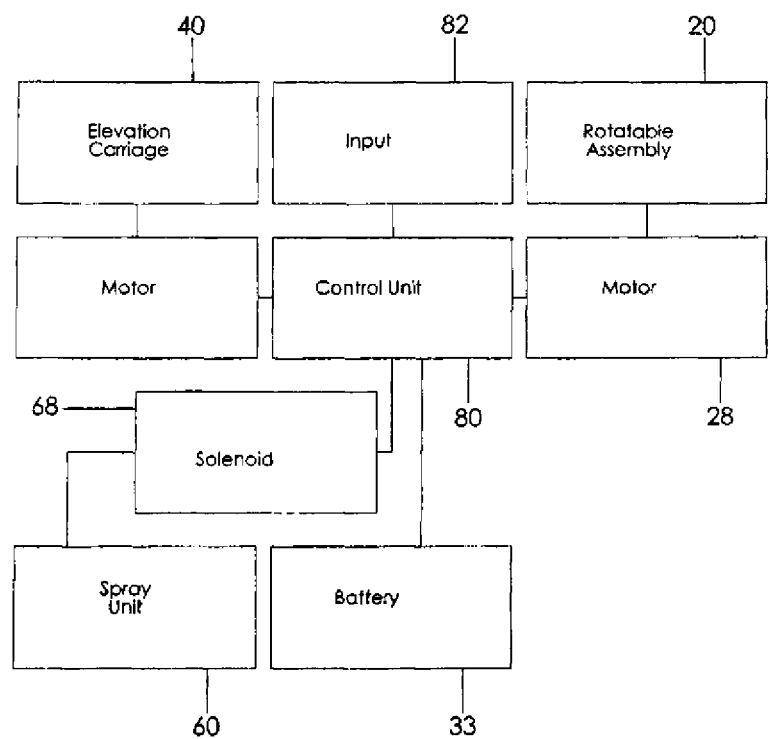
Figure 6:
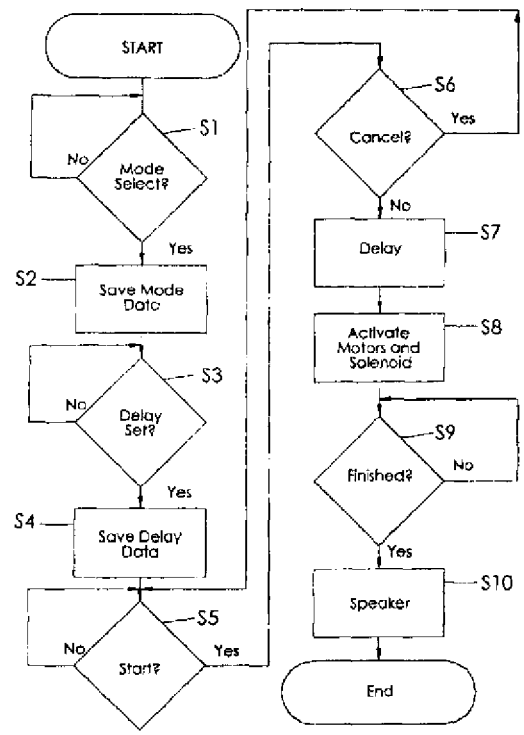

Specifically, at step S1, the control unit 80 determines if a user has selected a mode, such as by pressing the input 82 one or more times (FIG. 6). A "mode" refers to a predetermined time cycle for dispensing an amount of disinfectant. For instance, a small, medium, or large canister of disinfectant may be loaded into the delivery unit 60 and then the input 82 may be pressed an appropriate number of times corresponding to the time needed to dispense the disinfectant within the canister. If the input 82 has been pressed, the control unit 80 proceeds to step S2 where it saves the mode data and proceeds to step S3. If not, the control unit 80 just loops to continue waiting for the mode data. At step S3, the control unit 80 determines if a user has used the input 82 to submit a desired delay to be executed between a request to start a disinfectant dispensing cycle and its actual activation. In other words, when a user uses the input 82 to activate the first motor 28, second motor 50, and solenoid 68 to begin dispensing disinfectant, the control unit 80 will delay the activation to enable the user to leave the room and avoid contact with the disinfectant. At step S3, the control unit 80 determines if a user has used the input 82 to set this parameter which is referred to herein as "delay data." If so, the control unit 80 saves the delay data at step S4 and proceeds to step S5. Otherwise, the control unit 80 will loop at step S3 until this parameter is received.

At step S5, the control unit 80 determines if the input 82 has been operated to activate a dispensing cycle. If so, then the control unit 80 proceeds to step S6 and determines if the input 82 has been further operated to cancel the dispensing cycle. For example, the control unit 80 may check to see if a respective input 82 is operated within, say, 5 seconds to indicate that the first operation thereof was unintended and is desired to be canceled. If activation is not canceled, then the control unit 80 proceeds to step S7 to carry out the requested delay data, which gives a user an opportunity to leave the room. Then, control proceeds to step S8 in which the first motor 28, second motor 50, and solenoid 68 are activated. In other words, the rotatable assembly 20 and carriage 40 are activated to move as described above and the solenoid 68 is activated to cause the delivery unit 60 to dispense disinfectant as described above. If, however, activation is canceled at step S6, then control is returned to step S5 until activation is determined again by the input 82. At step S9, the control unit 80 determines if the dispensing cycle is finished (i.e. the cycle time indicated by the mode data has expired). If not, then the control unit 80 allows activation to continue and checks again. If, however, the cycle is finished, such as by expiration of a time associated with the mode data or by operation of the limit switch 48, control is passed to step S10 and a speaker is actuated to emit a tone or other sound indicative of completion of the cycle. This would signal a user that it is safe to enter the room.

In use, the disinfectant dispenser 10, when activated, causes a canister of disinfectant liquid or gas under pressure to be dispensed through the outlet nozzle 70 as described above. Simultaneously, the nozzle of the delivery unit 60 is rotated in a circular motion by operation of the rotating assembly 20 while the delivery unit 60 is pivoted between a vertical configuration and a horizontal configuration. Therefore, disinfectant may be distributed comprehensively and evenly throughout a room. It is understood that the dispenser described above would also be suitable for use in dispensing insecticides, pesticides, or other propellants.

It is understood that while certain forms of this invention have been illustrated and described, it is not limited thereto except insofar as such limitations are included in the following claims and allowable functional equivalents thereof.

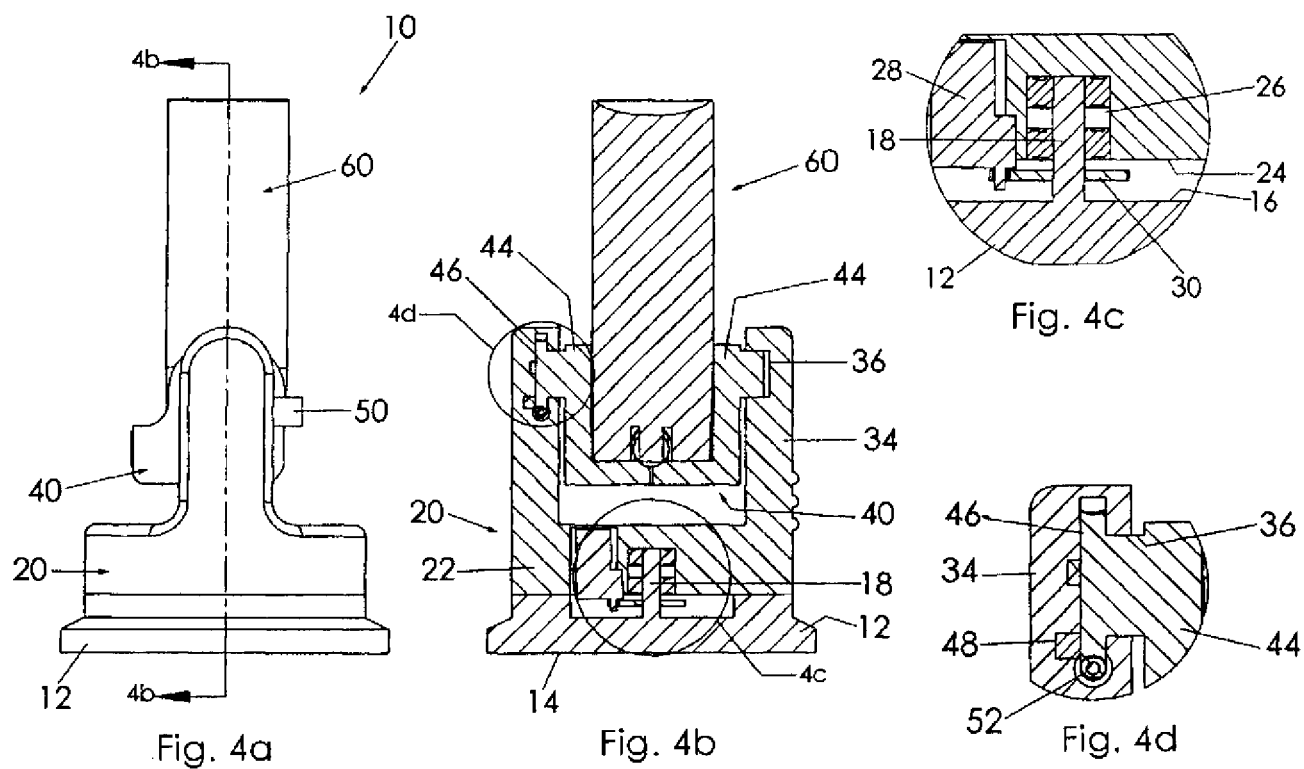

What is claimed is:

1. A rotary and elevation changing dispenser, comprising:
    a base;
    a rotating assembly coupled to said base and rotationally movable thereabout;
    a first motor operatively coupled to said rotating assembly for rotating said rotating assembly relative to said base when activated;
    a carriage pivotally connected to an upper portion of said rotating assembly and movable between vertical and horizontal configurations;
    a second motor operatively connected to said carriage for moving said carriage between said vertical and horizontal configurations when activated;
    a power source electrically connected to said first and second motors;
    a control unit electrically connected to said power source and to said first and second motors for selectively activating said first and second motors;
    a delivery unit mounted to said carriage and movable therewith, said delivery unit defining an interior area configured to receive a pre-packaged propellant and an outlet in communication with said interior area through which said propellant is propelled when activated;
    a solenoid proximate said delivery unit and electrically connected to said control unit and to said power source, said solenoid being configured to activate said propellant to be dispensed through said outlet when activated.

2. The dispenser as in claim 1, wherein:
    said base includes a mounting shaft extending upwardly from said base;
    said rotating assembly includes a mounting structure operatively coupled to said shaft for rotation thereabout when said first motor is activated; and
    said mounting structure is operatively coupled to said first motor and to said power source.

3. The dispenser as in claim 1, wherein:
    said rotating assembly includes a pair of spaced apart upstanding support arms;
    said carriage includes a body portion and a pair of divergent fasteners extending upwardly from said carriage body portion and pivotally coupled to respective support arms such that said carriage is selectively pivotal about an imaginary axis extending between said pair of fasteners; and
    said second motor is positioned on a respective rotating assembly support arm and operatively connected to a respective carriage fastener so as to move said carriage between said vertical and horizontal configurations when activated.

4. The dispenser as in claim 3, wherein said respective carriage fastener includes a worm gear operatively coupled to said second motor and configured to control a speed at which said carriage is moved between said vertical and horizontal configurations.

5. The dispenser as in claim 4 wherein said power source is a battery.

6. The dispenser as in claim 5, further comprising:
    a control unit electrically connected to said battery, said first motor, said second motor, and said solenoid;
    an input electrically connected to said control unit that is configured to receive at least one of mode data, delay data, and cancellation data.

7. The dispenser as in claim 6, further comprising a speaker electrically connected to said control unit, said control unit including means for actuating said speaker to emit an audible sound upon completion of a cleaning event.

8. The dispenser as in claim 4, wherein said respective carriage fastener includes a limit switch configured to halt movement of said carriage when said delivery unit is at a substantially horizontal configuration.

9. The dispenser as in claim 3, wherein:
    said solenoid is electrically connected to said power source and to said control unit situated on said carriage body portion in proximity to said delivery unit; and
    said delivery unit defines an aperture aligned with said solenoid and configured to receive said solenoid therethrough when said solenoid is activated so as to activate said propellant in said delivery unit interior area.

10. The dispenser as in claim 6, wherein said control unit is electrically connected to said input and includes programming for actuating said first motor, said second motor, and said solenoid for an amount of time associated with said mode data received from said input.

11. The dispenser as in claim 10, wherein said control unit includes programming to delay activation of said solenoid, said first motor, and said second motor according to said delay data received from said input.

12. The dispenser as in claim 11, wherein said control unit includes programming to cancel activation of said first motor, said second motor, and said solenoid upon receipt of cancellation data from said input.

13. The dispenser as in claim 12, wherein said control unit includes programming to actuate a speaker to enunciate a tone indicative of a cycle completion.

* * * * *

UNITED STATES PATENT AND TRADEMARK OFFICE
CERTIFICATE OF CORRECTION

PATENT NO. : 8,608,032 B2  
APPLICATION NO. : 12/957579  
DATED : December 17, 2013  
INVENTOR(S) : Susan M. Wolosuk Page 1 of 8

It is certified that error appears in the above-identified patent and that said Letters Patent is hereby corrected as shown below:

On the title page, replace the informal drawing with the formal drawing of Fig 1 as shown below.

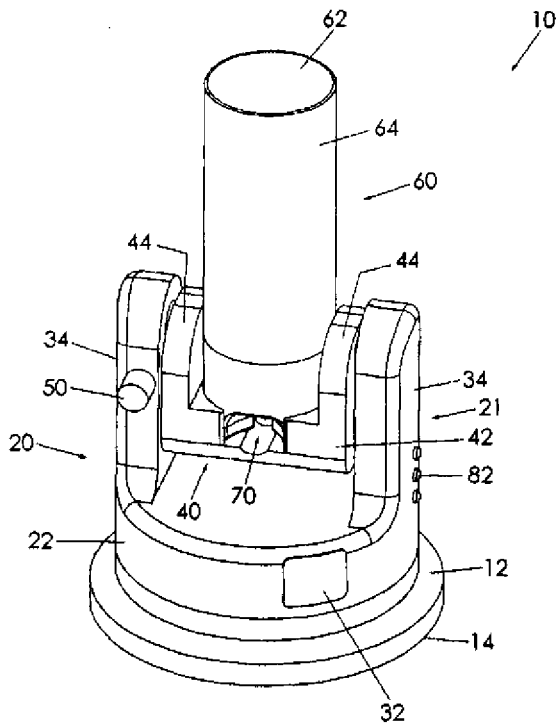

Signed and Sealed this  
Eighteenth Day of March, 2014

Michelle K. Lee  
*Deputy Director of the United States Patent and Trademark Office*

CERTIFICATE OF CORRECTION (continued)
U.S. Pat. No. 8,608,032 B2

In the Drawings

On drawing Sheet 1 of 6, replace the informal drawing of Fig. 1 with formal drawing of Fig. 1. (attached)

Figure 2:
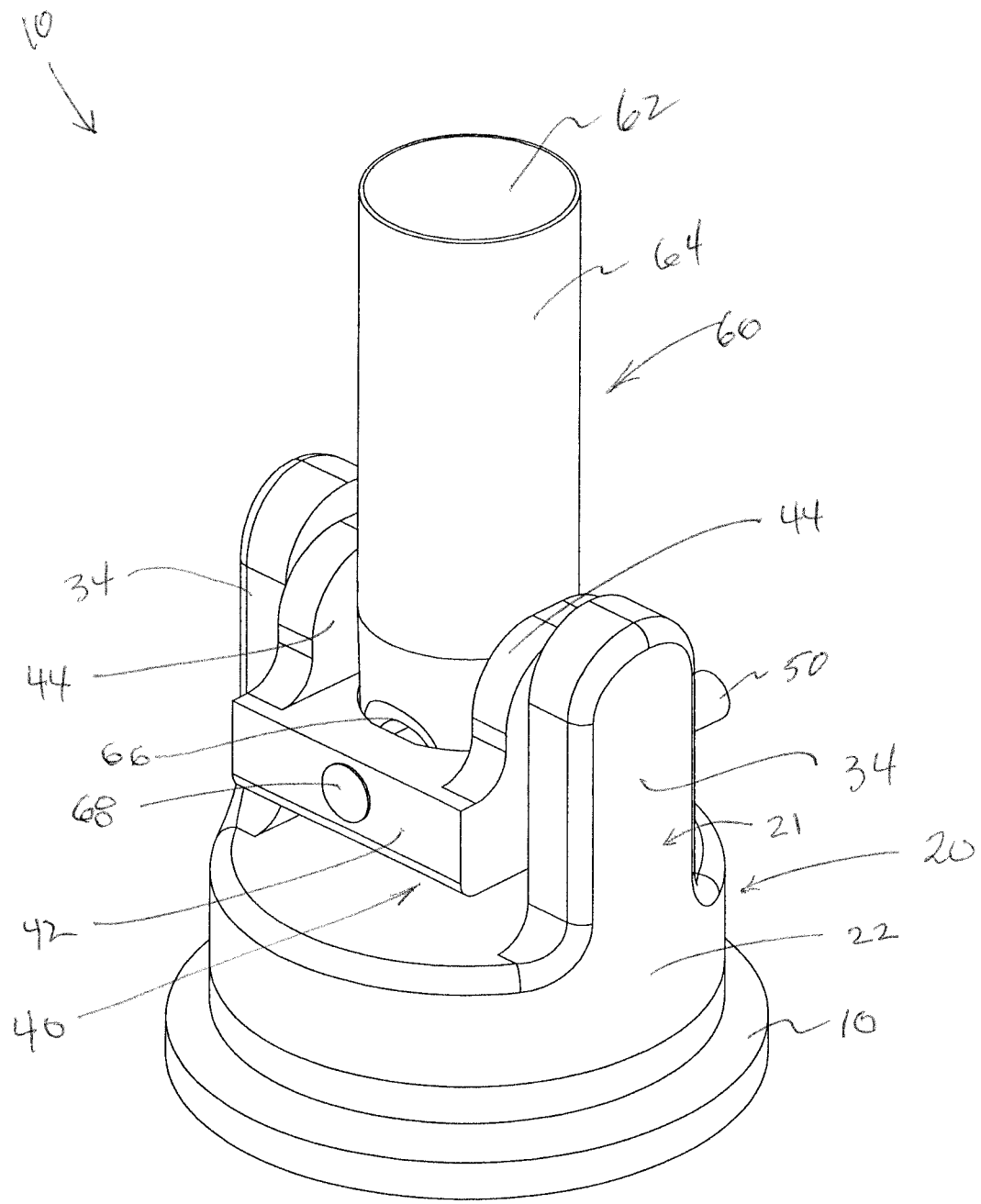
FIG. 2 is a perspective view of the dispenser as in FIG. 1 from another angle.

On drawing Sheet 2 of 6, replace the informal drawing of Fig. 2 with formal drawing of Fig. 2. (attached)

Figure 3A:
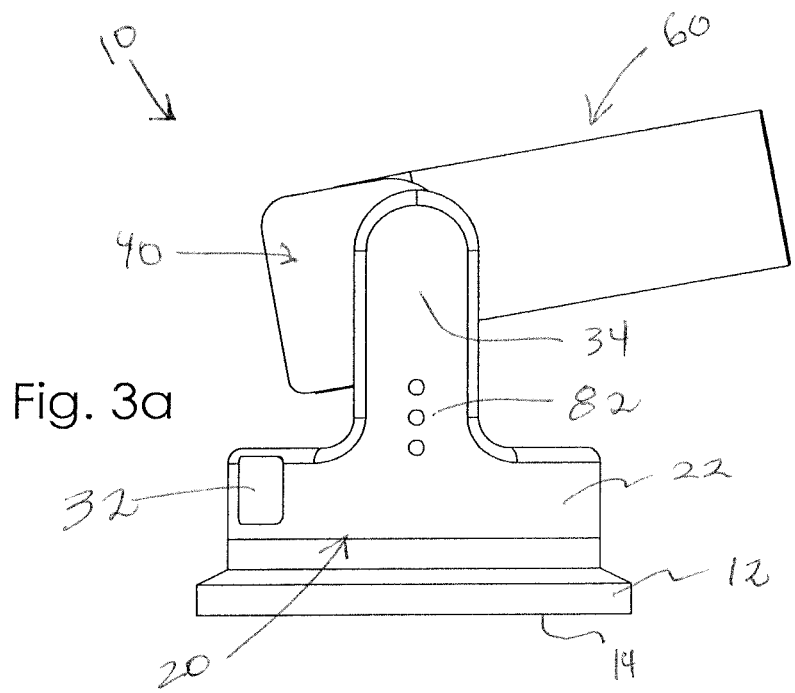
FIG. 3a is a side view of the dispenser as in FIG. 1 with the carriage at a substantially horizontal configuration.
Figure 3B:
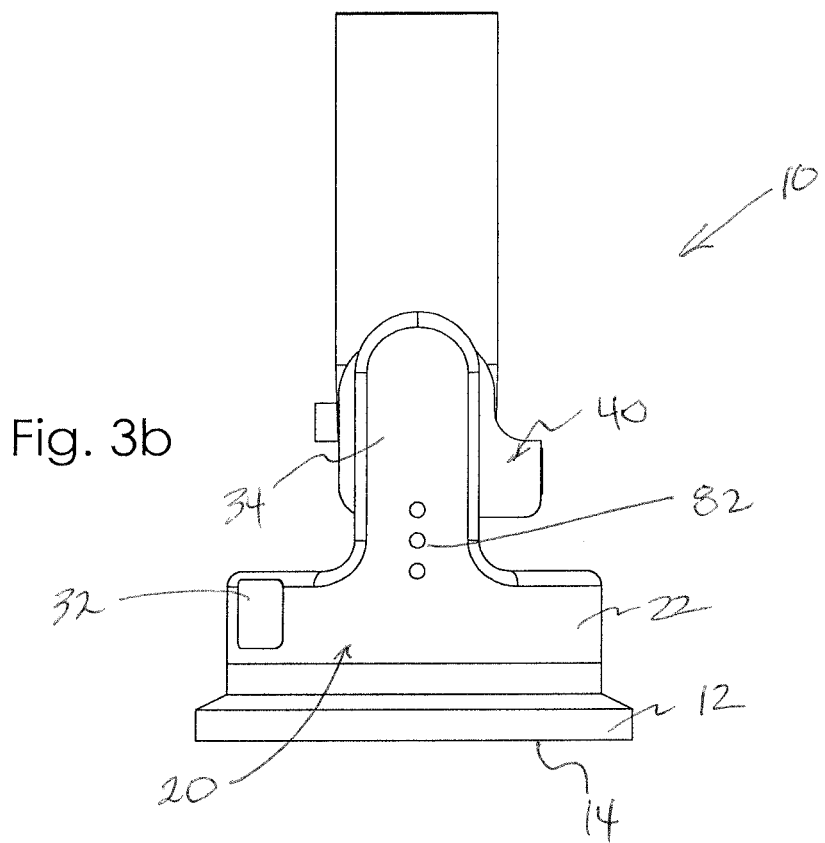
FIG. 3b is another side view of the dispenser as in FIG. 1 with the carriage at a substantially vertical configuration.

On drawing Sheet 3 of 6, replace the informal drawings of Fig. 3a and Fig. 3b with formal drawings of Fig. 3a and Fig. 3b. (attached)

On drawing Sheet 4 of 6, replace the informal drawings of Fig. 4a, Fig. 4b, Fig. 4c, and Fig. 4d with formal drawings of Fig. 4a, Fig. 4b, Fig. 4c, and Fig. 4d. (attached)

On drawing Sheet 5 of 6, replace the informal drawing of Fig. 5 with formal drawing of Fig. 5. (attached)

On drawing Sheet 6 of 6, replace the informal drawing of Fig. 6 with formal drawing of Fig. 6. (attached)